(12) United States Patent
Ahn et al.

(10) Patent No.: US 9,333,320 B2
(45) Date of Patent: May 10, 2016

(54) OPEN TYPE EAR TREATMENT MODULE

(75) Inventors: Jin Chul Ahn, Gyeonggi-do (KR); Chung Ku Rhee, Chungcheongnam-do (KR); Pill Sang Chung, Chungcheongnam-do (KR); Myung Whan Suh, Seoul (KR)

(73) Assignee: Industry-Academic Cooperation Foundation, Dankook University, Gyeonggi-Do (KR)

( * ) Notice: Subject to any disclaimer, the term of this patent is extended or adjusted under 35 U.S.C. 154(b) by 422 days.

(21) Appl. No.: 13/988,957

(22) PCT Filed: Nov. 22, 2011

(86) PCT No.: PCT/KR2011/008937
§ 371 (c)(1),
(2), (4) Date: Aug. 1, 2013

(87) PCT Pub. No.: WO2012/070851
PCT Pub. Date: May 31, 2012

(65) Prior Publication Data
US 2013/0303838 A1    Nov. 14, 2013

(30) Foreign Application Priority Data

Nov. 22, 2010    (KR) .................. 10-2010-0116447

(51) Int. Cl.
*A61N 5/06*  (2006.01)
*A61M 21/02*  (2006.01)
*A61F 11/00*  (2006.01)
*A61H 39/00*  (2006.01)

(52) U.S. Cl.
CPC ................ *A61M 21/02* (2013.01); *A61F 11/00* (2013.01); *A61N 5/06* (2013.01); *A61N 5/0622* (2013.01); *A61H 2039/005* (2013.01); *A61H 2205/027* (2013.01); *A61N 2005/0605* (2013.01)

(58) Field of Classification Search
USPC ............... 381/324–326; 607/88, 89; 600/301, 600/25–28
See application file for complete search history.

(56) References Cited

U.S. PATENT DOCUMENTS

2010/0217102 A1 *   8/2010   LeBoeuf .................. A61B 5/00
                                                                600/310

FOREIGN PATENT DOCUMENTS

| JP | 2003225313 | 8/2003 |
| KR | 200328968 | 10/2003 |
| KR | 200396118 | 9/2005 |
| KR | 100715032 | 5/2007 |

OTHER PUBLICATIONS

International Search Report for International Application No. PCT/KR2011/008937 dated May 22, 2012.

* cited by examiner

*Primary Examiner* — William Thomson
*Assistant Examiner* — Jeffrey Lipitz
(74) *Attorney, Agent, or Firm* — Fitch, Even, Tabin & Flannery, LLP

(57) ABSTRACT

The present invention relates to an open type ear treatment module which, when worn, allows simultaneous laser therapy and music therapy for brain-nervous system tissue by arranging the light source for low level laser therapy (LLLT) and sound source for music therapy (MT) properly, and can release the heat generated by the light source to outside by allowing ventilation with outside through open type configuration of module itself.

7 Claims, 2 Drawing Sheets

OPEN TYPE EAR TREATMENT MODULE

CROSS REFERENCE TO RELATETED APPLICATIONS

Figure 1:
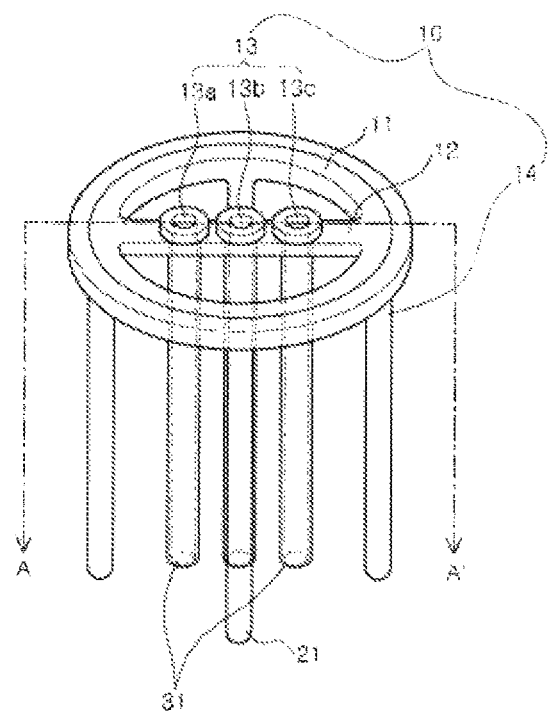

This application is a national phase application of International Application No. PCT/KR2011/008937, filed Nov. 22, 2011, and claims priority to Korean Patent Application No. 10-2010-0116447, filed Nov. 22, 2010, both of which are incorporated by reference herein in their entirety.

TECHNICAL FIELD

The present invention relates to an open type car treatment module and more specifically to an open type ear treatment module which, when worn, allows simultaneous laser therapy and music therapy for brain-nervous system tissue by arranging the light source for low level laser therapy (LLLT) and sound source for music therapy (MT) properly, and can release the heat generated by the light source to outside by allowing ventilation with outside through open type configuration of module itself.

BACKGROUND ART

In modern medicine, laser has been used in the various form. Medical application of laser, which was limited to the surgical area, has been widely extended to non-vascular diagnostic and therapeutic areas in recent years. First, laser was unreduced into surgical procedure and laser introduced into surgical area has high output energy and functions tissue destruction. High level laser was applied, through the tissue destruction phenomenon, to tissue cutting, coagulation and hemostasis. Then, low level laser therapy began to be applied to the treatment of wound at first. Researches for clinical effect and photobiological, photochemical reaction of low level laser have been carried on, reported on healing of damaged tissues, analgesic effect, anti-inflammatory effect, anti-edema effect, tissue vascular change and stimulation effect on the cell, and low level laser is used in many areas of medicine, as examples, in treatment of wound, tissue defects, etc. in dermatology, inner ear diseases, ear infections, etc. in otolaryngology, bruises, contusion, etc. in acupuncture, aphthous stomatilis, gingivitis, etc. in dentistry, rheumatoid arthritis, sprains, etc. in orthopedics.

In the case such as arthritis or dermatitis, while current treatment method in the form of medicated patch put on the affected area such as or medicine for oral administration have side effects such as festering of affected area or gastrointestinal dysfunction when used for long period and are less effective due to passive delivery of efficacy, method to project the laser light, which is not in direct contact with human body, doesn't have a side effect of festering of affected area and the treatment effect can be maximized by using algorithm which can generate the laser light creating proper treatment effect when projected to the affected area.

Meanwhile, photochemical action for plant can be observed in carbon dioxide assimilation and for the living body, it has been known that when illuminating light. APT is produced by the optical action and cells are activated. In other words, laser light, if illuminated on the living body with low energy not to burn in-vivo cells, has effects in activating the physiological function of living body and promoting natural healing power of affected area, which has been well known in the medical field through experiences in surgical procedure already having used high level laser.

Recently, low level laser therapy (LLLT) has been developed to treat various diseases actively using this action and begins to be used in several disease areas.

Biochemical action of light is depends on wavelength, polarization, and intensity of light and, according to experimental results, it has been known that polarized light with energy of around 100 $m^W$ in the range of 600 um ~1000 um has the greatest effect on human body.

Such light can be generated using He~Ne laser, semiconductor laser or YAG laser with semiconductor laser being favorable in terms of size or price, and now semiconductor laser with GaAs (904 nm), GaAlAs (780-820-870 nm), InGaAlP (630-685 nm) as material is mainly developed and sold.

However, emitted light of LED has been reported to be available instead of laser, and is adopted in the product which regards especially production cost as important. Although beam width of LED can not be narrowed below the certain level and it is not polarized because LED is not a coherent light as a laser. LED generates the light of the range of 600~1000 nm and can produce similar effect when semiconductor laser is used as long as the intensity of around 100 $m^W$/cm is guaranteed.

Currently, the most prevalent in the low level laser therapy (LLLT) are the various pain treatments, which was greatly developed because of the large effects on elimination of pain discovered after Prof. Plog, Canada examined the He—Ne laser on the meridian point as the form of laser acupuncture.

Researches for clinical effect and photobiological photochemical react ion of low level laser have been carried on, reported on healing of damaged tissues, analgesic effect, anti-inflammatory effect, anti-edema effect, tissue vascular change and stimulation effect on the cell, and low level laser is used in many areas of medicine.

However, conventional form of laser therapy device is treated as medical equipment and large in volume so that is can be used restrictedly in certain medical institutions such as hospitals or health centers, and has a drawback of large production cost.

In addition, the range of illumination of laser light doesn't reach deep into the inside, and therefore there is an difficulty in effective treatment.

Furthermore, the existing devices comprise the structure wherein the earpiece fastened to the ears is blocked from the outside, and has an disadvantage of inflammation in the inner ear caused by the heat generated by laser, due to no ventilation with the air.

DISCLOSURE

Technical Problem

The objective of the present invention to solve the above problems is to provide an open type ear treatment module which, when worn, can prevent or treat inner ear diseases, otitis media by performing optical therapy and music therapy at the same time by placing the light source for low level laser therapy and sound source for music therapy in the first hole, the second hole and the third hose and illuminating to the external auditory canal.

The present invention also provides an open type ear treatment module which allows treatment through procedure and is not restricted by the place by installing the light source and sound source on the ear piece wearable on auricle and external auditory canal.

The present invention also provides an open type ear treatment module which prevent inflammation caused by the heat generated by laser by introducing the structure with easy ventilation with outside through multiple guide braces fastened in contact with external auditory canal.

Technical Solutions

In order to resolve the above problems, an open type ear treatment module of the present invention comprises the mounting unit in the hollow part; a bar connecting the inner parts of the mounting unit; one or more holes formed on the bar; light output unit inserted and fastened to the one or more holes; and the light source which can transmit the light to the light output unit, which receives the light from one or more of laser diode or light emitting diode and illuminates the light to the inside of external auditory canal.

The open type ear treatment module comprises sound output unit inserted an fastened to the one or more holes; and sound source which can transmit the sound to the sound output unit, which receives the sound from the sound source and transmit the sound to the inside of external auditory canal.

The light output unit comprises being inserted and fastened to the hole which is located in the center among the above holes.

The open type ear treatment module comprises further the coupling line, which couples the light source to the light output unit and consists of the optical fiber.

The light source comprises the monochromatic light from ultraviolet rays below 400 nm or infrared rays above 750 nm.

The sound source comprises the one or more sounds of nature such as sound of birds or sound of waves.

The open type ear treatment module further comprises one or more guide braces which are formed in extension of one side of the mounting unit at a predetermined distance, wherein the guide brace is positioned radially from the center of the mounting unit.

As the materials of the mounting unit and guide brace, one or more can be used from silicone, polyurethane, rubber.

Effect of Invention

According to the present invention, as above-mentioned, illumination of laser light intensively into external auditory canal by inducing laser light with optical fiber has the effect on treatment of various diseases that occur in the ear.

Also, the present invention provides patients with psychological stability by illuminating the laser light by the light source at the same time while applying music therapy (MT) and therefore the synergistic effect of the treatment can be expected.

In addition, the present invention has an effect on no restriction of place by installing the light source and sound source on the ear piece wearable on auricle and external auditory canal.

Furthermore, according to the present invention, introduction of open type configuration of the module itself which allows the easy ventilation with outside has an effect on prevention of inflammation caused by the heat generated by laser.

DESCRIPTIONS OF FIGURES

Figure 2:
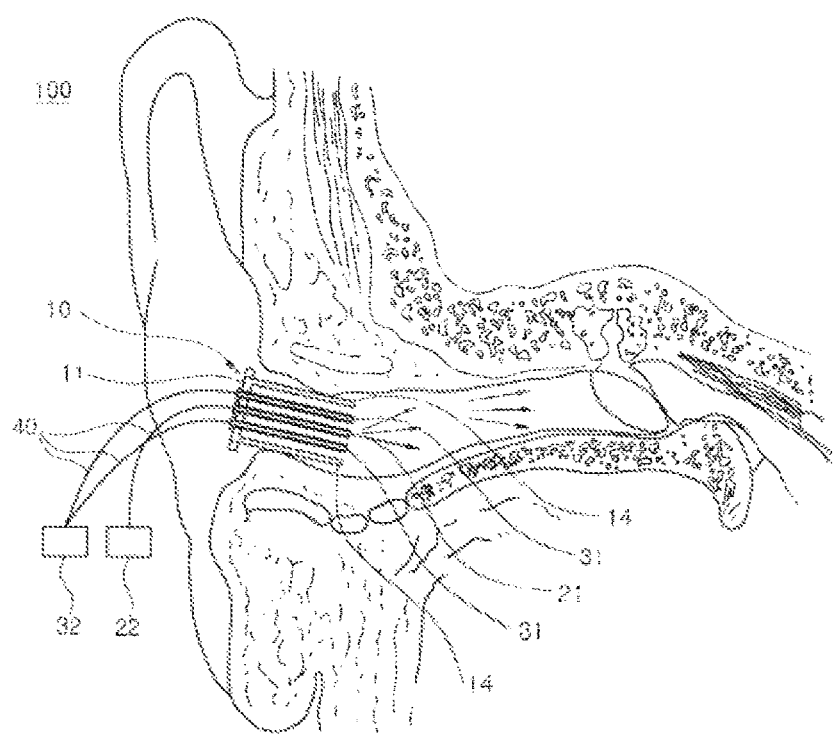

FIG. 1 is a perspective drawing of an open type ear treatment module according to an example of the present invention, and FIG. 2 is a cross-sectional drawing of an open type ear treatment module according to an example of the present invention while put on the ear.

SPECIFIC MODE OF INVENTION

Preferable example of an open type ear treatment module according to the present invention is described with reference to FIGS. 1 to 2. The thickness of lines or size of components illustrated so the drawings in this process may be shown exaggerated for convenience and clarity of explanation. In addition, the terms used herein are defined by considering the features of the present invention, and can vary depending on the intentions of users, operators, or custom. Therefore, the definition of these terms will be described on the basis of the information throughout the present full statement.

For laser applied to an open type ear treatment module according to the present invention, although low level laser therapy (LLLT) is described as one example, it is to be noted that the scope of the application of laser is not limited to the low level laser therapy and another method that can be applied.

An open type ear treatment module (100), according to the present invention, comprises an earpiece (10) seated on the ear canal and the auricle, the ear piece (10) which has the form of the center of the light source (20), a sound source (30) which has the form of the lateral sides of the light source (20) and the light source (20) and sound source (30), the light source (20) and the sound source (30) each of which communication consists of a coupling line (40).

In the following, the open type ear treatment module (100) is described in more detail.

An earpiece (10) consists of mounting unit (11), bar (12), hole (13) and guide brace (14).

A mounting unit (11) has a hollow cylindrical shape. Preferably, a mounting unit (11) is to be used as tailored to the individual's ear shape in order to put on the user's ear and be seated in the auricle and external auditory canal. In the present invention, a mounting unit (11) is illustrated and described as hollow cylindrical shape, it is to be noted that it can be designed to fit the user's intent and use without any restriction of the shape.

In addition, mounting unit (11) is worn in contact with the skin, and therefore for the material thereof, it is preferable to use silicon which causes little trouble to the skin and has high elasticity. Such a mounting unit (11) is seated in the auricle of outer ear, allows the smooth ventilation with the air and can prevent inner ear diseases and otitis media.

Bar (12) is formed to pass through the center of the mounting unit (11) and connect between the inner circumferences. Bar (12) acts as structural support for the cylindrical mounting unit (11), and one or more holes (13), which will be described later, are formed on the bar.

One or more holes (13) may consist of the first hole (13a), the second hole (13b), and the third hole (13c).

One or more holes (13) are formed on and through the bar (12), in order of the first hole (13a), the second hole (13b), and the third hole (13c) from one side. The present invention, as illustrated in FIG. 2, comprises the first hole (13a), the second hole (13b), and the third hole (13c), but different number of holes can be naturally formed by considering the range of illumination of light source (20), range of transmission of sound source (30), etc.

The first hole (13a) is formed first from one side of the bar (12), and the sound source (30) which will be described later may be fastened to the first hole (13a).

The second hole (13b) is formed from one side of the first hole (13a), and the light source (20) which will be described later may be fastened to the second hole (13b).

The third hole (13c) is formed from one side of the second hole (13b), and the sound source (30) which will he described later may be fastened to the third hole (13c).

The present invention comprises the light source (20) fastened to the second hole and the sound source (30) fastened to the first hole (13a) and the third hole (13c), but it is to be noted that separate light source can be fastened to the first hole (13a) and the third hole (13c) as necessary to increase the efficiency of irradiation. Moreover, in this case, the light source fastened to each hole, by having different wavelength bands, allows a more effective treatment.

In the present invention, as illustrated in FIG. 2, the first hole (13a), the second hole (13b), and the third hole (13c) are formed in order from the one side of rectilinear bar which passes through the center of mounting unit (11) and connects between inside of the mounting unit (11), multiple holes (13) such as the first hole (13a), the third hole (13c), and fourth hole (not illustrated) can naturally formed radially around the second hole (13b) located in the center of bar (12).

The guide braces are formed in extension of bottom surface of the mounting unit at a predetermined distance, and preferable at regular intervals on the perimeter of bottom surface of the mounting unit. In particular, four guide braces (14) are illustrated in FIG. 1 of the present invention, but multiple may be formed as necessary in the process of being seated in the external auditory canal through ear canal through auricle.

Also, the material of the guide brace (14) can be selected from one or more of silicone, polyurethane, rubber.

The guide braces (14) are aide to enter smoothly into the inside of external auditory canal the guide braces, which entered into the inside of external auditory canal, are seated closely to the external auditory canal due to high elasticity.

Such a structure, unlike the conventional inventions of all-in-one configuration, allows the space between the guide braces (14), expands the region where the light source (20) and the source (30) are transmitted to the external auditory canal, and has an advantage of improvement of treatment effect.

The light source is inserted and fastened to the second hole (13b) and arranged horizontal to the mounting unit (11). As the light source, any one of laser diode or light emitting diode can be selected.

Light output unit (21) serves for receiving the light transmitted from the light source (20) and transmitting the light to the inside of external auditory canal.

It is well known that, if low level laser light as not to harm to the surface of the body is illuminated on the human body through the light source (20) as described above, the metabolism of the cell in the illuminated area becomes active and immunity increases by the photochemical effect, having effects in prevention of disease, would healing, removal of pain.

This process, wherein light energy of a specific wavelength is absorbed into the tissue in vivo and excited at the molecular and cellular level, exhibits the effects on increasing creation of the capillaries, increasing amount of oxygen loading of blood, facilitating the creation of collagen and APT, increasing lymphatic activity, facilitating the creation of granulation, activating phagocytosis, and therefore low level laser therapy (LLLT) using such effects has attracted attention in various fields. The wavelength of light used here is chosen usually in the range of 600~1000 um by considering the size of the heating effects on the biological tissue, transmissivity, and photochemical effects.

For example, the direct illumination of light output of the laser diode or LED device of wavelength of around 600~1000 um at the intensity of around 100~1000 mW on the surface of the body can be applied to the above therapy. As a light emitting device, a semiconductor laser diode (LD) or light emitting diode (LED) can be used. The combination of them with a large number, certainly, can be applied as a surface light source as well.

In addition, direct illumination on the affected area as well as meridian points is identified to have excellent effect in healing the disease itself as well as pain, and application field thereof is being greatly expanded. In particular, it has the excellent effect in various chronic diseases known as incurable, and the technique is essentially non-surgical and drugless, also accompanies virtually no patient's pain nor side effect and costs extremely less compared to the conventional therapy method.

Meanwhile, photodynamic therapy (PDT) is developing along with immunotherapy, gene therapy as another treatment method for various cancers in addition to three main treatment methods of cancer such as surgery, chemotherapy and radiation therapy. Photodynamic therapy (PDT) is the next-generation therapy, wherein a single oxygen and free radical caused by chemical reaction of photosensitizer by light and oxygen destroy cancer cells selectively without any pain to the patient.

Sound source (30) is inserted and fastened to the first hole (13a) and the third hole (13c), and arranged horizontal to the mounting unit (11).

It is preferable for the patient to listen to the sound source (30) selected from music, or any sound of nature such as sound of birds, or sound of waves, which relieves physical and mental stress, and promotes the natural healing power of the body.

Music therapy using the sound source (30) utilizes the effect of psychological satisfaction when listening to the well-played music on the various physiological phenomena, i.e., the relaxation of each organ tissue, increase of endocrine such as entropy, increase of bloodstream and decrease of blood pressure, which aid in recovering fatigue, settling the nerve, and stabilizing the pain, and promote prevention of disease and natural healing.

A sound output unit is the device for outputting the sound generated form the sound source (30) and serves for transmitting the sound to external auditory canal.

A coupling line (40) is connected to light source (20) and sound source (30), separately. Preferably, coupling light (40) is forced with two or more.

A coupling line (40) connected to light source (20) serves for transmitting the laser light which is transmitted to the light source (20) through the coupling line, and the laser light emitted from the light source is illuminated to external auditory canal.

As a coupling line (40) connected to light source (20), it is preferable to use the optical fiber which consists of glass with high refractive index in the central portion and glass with low refractive index in the outer portion so that the light passing trough the glass in the central portion is totally reflected.

As the optical fiber, it may be preferable to choose one of glass optical fiber (GOF) with a two-layer structure of core of high refractive index and clad of low refractive index, which utilizes the principle of light being received from one end and transmitted to the other end through total reflection between core and clad, or plastic optical fiber (POP) which is similar to optical fiber but consists of core of high purity PMMA (poly methyl methacrylate) and clad of high-purity F-PMMA (fluorinated PMMA).

In addition, the sound of nature is transmitted to sound source (30) through coupling line (40), and sound of nature transmitted to sound source (30) is transmitted to external auditory canal, promotes the psychological stability and adds to the effect by being applied simultaneously with the low level laser therapy by the light source (20).

An open ear treatment module (100) according to the present invention, as described above, can perform acupuncture therapy which can treat various dysfunctions of the body, including the brain-nervous system disorders, by simulating the multiple meridian points, comprising acupuncture points in the in the temporal region including the ear, through illuminating laser light from the light source (20) effectively to the external auditory canal, which is one of the region without skull in the head.

In addition, since the various stimuli on the human body are known to have synergistic effects on healing the certain conditions, synergistic effect of two effects by simultaneous application of low level laser therapy and music therapy can be expected.

Although the present invention is described with reference so the example in the above, those skilled in the art wall understand that the present invention can be changed and modified variously within the concept and scope concept of the present invention described in the claims in the following.

The invention claimed is:

1. An open type ear treatment module comprising:
    an earpiece configured for disposition in an ear of a user;
    a light source providing a light for low level laser therapy into the external auditory canal of the ear through the earpiece; and
    a sound source providing sound music therapy into the external auditory canal of the ear through the earpiece;
    wherein the earpiece comprises:
    a mounting unit seated in the auricle of the ear and having a hollow cylindrical shape;
    a bar connected to the inner circumference of the mounting unit and disposed to pass through the center of the mounting unit, the bar having a plurality of holes formed through the bar; and
    a plurality of output units coupled to the plurality of holes, each output unit having a pipe shape and one end inserted into a corresponding hole of the plurality of holes,
    wherein the light source is connected to one of the plurality of holes and the sound source is connected to another of the plurality of holes.

2. The open type ear treatment module, according to claim 1,
    wherein the light source is connected to a hole which is located in the center of the bar among the plurality of holes.

3. The open type ear treatment module, according to claim 2,
    further comprising a coupling line, which connects the light source to the hole which is located in the center of the bar and comprises an optical fiber.

4. The open type ear treatment module, according to claim 2,
    wherein the light source comprises monochromatic light from ultraviolet rays below 400 nm or infrared rays above 750 nm.

5. The open type ear treatment module, according to claim 2,
    wherein the sound source comprises a sound of nature such as sound of birds, or sound of waves.

6. The open type ear treatment module, according to claim 1,
    further comprising one or more guide braces formed on one side of the mounting unit.

7. The open type ear treatment module, according to claim 6,
    wherein one or more of silicone, polyurethane, and rubber are used as materials for the mounting unit and one or more guide braces.

* * * * *